United States Patent [19]
Bock

[11] Patent Number: 5,353,546
[45] Date of Patent: Oct. 11, 1994

[54] COMBINATION VASE AND AIR FRAGRANCE DISPENSER

[76] Inventor: Ronald F. Bock, 4660 Dahlia Ave., St. Louis, Mo. 63116

[21] Appl. No.: 81,982

[22] Filed: Jun. 23, 1993

[51] Int. Cl.$^5$ .............................................. A01G 9/02
[52] U.S. Cl. ........................................ 47/66; 239/51.5
[58] Field of Search ............... 47/66 C, 66, 79, 79 C, 47/80, 81; 239/51.5

[56] References Cited

U.S. PATENT DOCUMENTS

| | | | |
|---|---|---|---|
| D. 149,252 | 4/1947 | Cobbs . | |
| D. 324,099 | 2/1992 | Weick . | |
| 102,311 | 4/1870 | Penfield | 47/80 |
| 661,411 | 11/1900 | Lonitz | 47/79 |
| 954,440 | 4/1910 | Klemm | 47/79 |
| 2,481,296 | 9/1949 | Dupuy | 239/51.5 |
| 2,529,536 | 11/1950 | Bjorksten | 239/51.5 |
| 2,807,901 | 10/1957 | Gilowitz . | |
| 3,330,481 | 7/1967 | Dearling | 239/51.5 |
| 3,400,890 | 9/1968 | Gould . | |
| 3,962,824 | 6/1976 | Poston . | |
| 4,034,507 | 7/1977 | Dedolph | 47/66 |
| 4,165,835 | 8/1979 | Dearling . | |
| 4,327,056 | 4/1982 | Gaiser | 239/51.5 |
| 4,525,950 | 7/1985 | Glassman . | |

FOREIGN PATENT DOCUMENTS

| | | | |
|---|---|---|---|
| 31580 | of 0000 | Fed. Rep. of Germany | 47/79 |
| 867180 | 2/1953 | Fed. Rep. of Germany | 47/80 |
| 95840 | 5/1939 | Sweden | 47/81 |
| 8588 | of 1896 | United Kingdom | 47/80 |

*Primary Examiner*—Ramon S. Britts
*Assistant Examiner*—Joanne C. Downs

[57] ABSTRACT

A combination vase and air fragrance dispenser comprised of two interconnecting vessels, one to hold natural or artificial flowers, the other to hold air treatment material and dissipate fragrance to the atmosphere. Its two-vessel construction makes it possible to completely separate flowers and air treatment material, preventing contamination of the flowers.

2 Claims, 4 Drawing Sheets

COMBINATION VASE AND AIR FRAGRANCE DISPENSER

BACKGROUND OF THE INVENTION

This invention relates to vases and air fragrance dispensers. More specifically, it relates to vases which combine the functions of holding natural or artificial flowers and fragrance dissipation.

There are many types of vases used for displaying artificial or natural flowers. However, natural flowers may have weak fragrances or soon lose their aromas, while artificial flowers have no fragrance. Previous inventions have utilized vase shapes for air fragrance dispensers, but have failed to provide a receptacle for flowers separate from the air treatment material. Therefore, a need exists for a display receptacle which can hold water needed to keep natural flowers fresh or display artificial flowers, while at the same time serving as a dispenser for air fragrance.

The present invention seeks to meet this need by combining the functions of vase and air fragrance dispenser, allowing either natural or artificial flowers to be attractively displayed, while simultaneously allowing for the use of liquid or solid air treatment material.

SUMMARY OF THE INVENTION

Accordingly, it is an object of this invention to provide a combination vase and air fragrance dispenser which can hold artificial flowers in a dry state, or alternatively hold water necessary for real flowers.

A further object of this invention is to provide separate vessels or containers for the air treatment material and the flowers, thus preventing contamination of the flowers.

Another object of this invention is to provide such a combination vase and air fragrance dispenser that is pleasant in appearance, simple and rugged of construction, and relatively inexpensive to manufacture.

These and other objects and advantages of this invention will become apparent from consideration of the drawings and description which follow.

The present invention could be constructed in a variety of aesthetically appealing vase shapes. Generally, it would consist of two separate vessels, the inner vessel for holding flowers, the outer vessel for holding liquid or solid air treatment material. The outer vessel has an upper and lower chamber, or space. The air treatment material is placed in the lower chamber. The upper portion of the outer vessel contains vent holes to allow the fragrance to be dissipated into the surrounding atmosphere. The removable inner vessel fits inside the outer vessel, and is sealed so that water cannot escape, nor can the flowers come in contact with the air treatment material.

If the invention were formed in the narrow, cylindrical shape of a bud vase, it would have an upper and lower vessel instead of an inner and outer vessel. The upper vessel would hold the flowers. It would fit on top of the lower vessel, where the air treatment material would be placed. The vent holes would be placed near the bottom of the upper vessel but below the sealed portion which holds the flowers.

REFERENCE NUMERALS IN DRAWINGS

10—Combination vase and air fragrance dispenser
12—Outer vessel
14—Top opening
16—Lip
18—Vent holes
22—Outer vessel upper chamber
24—Outer vessel lower chamber
26—Flowers
30—Inner vessel
32—Flanged collar
34—Inner vessel chamber
36—Inner vessel base
38—Inner vessel wall
40—Combination vase and air fragrance dispenser (alternate embodiment)
42—Upper vessel
44—Upper vessel lower opening
46—Lower lip
52—Upper vessel upper chamber
54—Upper vessel lower chamber
56—Chamber separator
60—Lower vessel
62—Inward flanged collar
64—Lower vessel chamber
66—Lower vessel opening

DETAILED DESCRIPTION OF ILLUSTRATIVE EMBODIMENT

Figure 1:
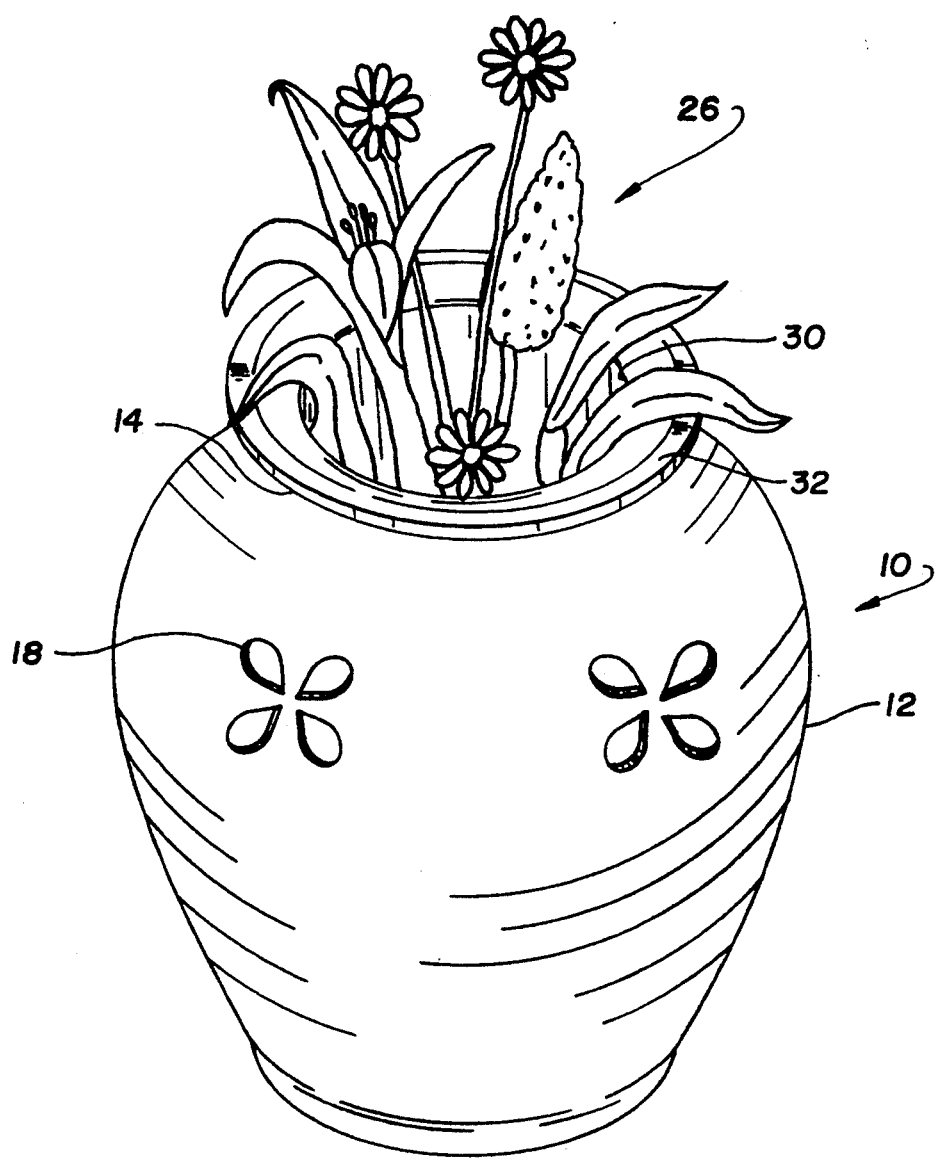
FIG. 1 is a perspective view of one embodiment of the combination vase and air fragrance dispenser which comprises the present invention.

FIG. 1 shows a combination vase and air fragrance dispenser 10 comprised of an outer vessel 12 and an inner vessel 30. Outer vessel 12 has a top opening 14, into which inner vessel 30 is inserted. Inner vessel 30 has a flanged collar 32 which is positioned over top opening 14. An assortment of flowers 26 protrudes upwardly from inner vessel 30. A plurality of vent holes 18 are positioned on the upper portion of outer vessel 12.

Figure 2:
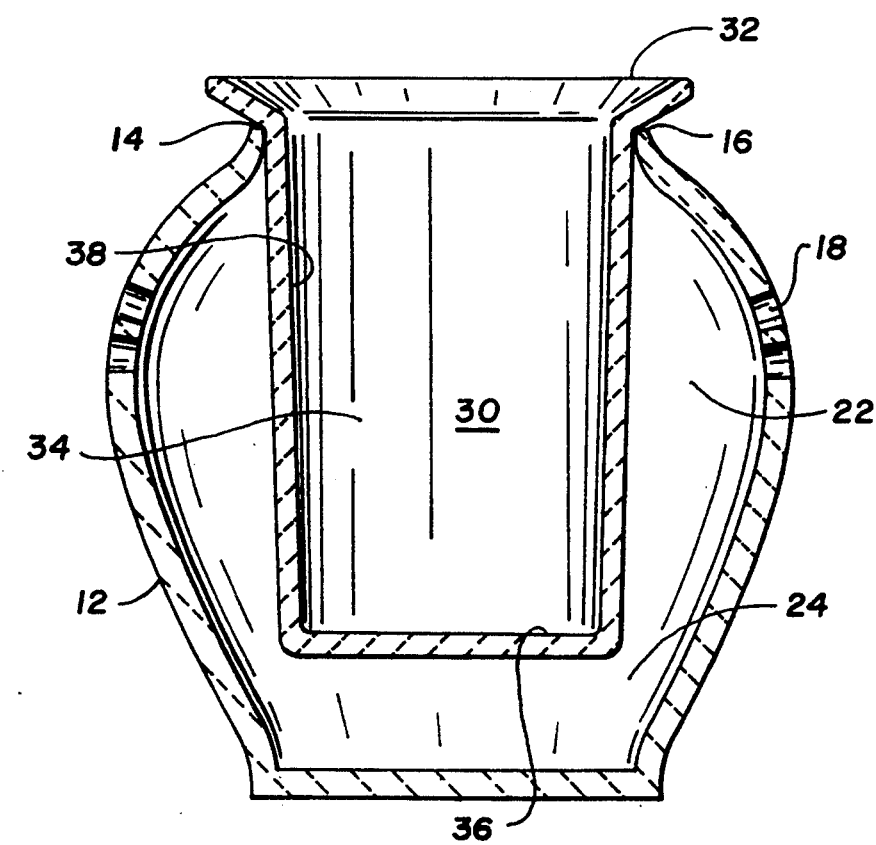
FIG. 2 is a vertical sectional view showing the construction.

As shown in FIG. 2, outer vessel 12 is comprised of an outer vessel lower chamber or space 24 where conventional liquid or solid air treatment material (not shown) may be placed, and an outer vessel upper chamber 22. The upper portion of outer vessel upper chamber 22 has a plurality of vent holes 18 to provide venting for fragrance from air treatment material to atmosphere. Within outer vessel 12 is located inner vessel 30 which has an inner vessel chamber 34 into which liquid, dirt, plants, flowers, or artificial flowers may be placed. Inner vessel 30 has an imperforate inner vessel wall 38 which terminates at its upper end in flanged collar 32. Flanged collar 32 fits over top opening 14 which is defined by a lip 16 of outer vessel 12. The lower end of imperforate inner vessel wall 38 has an imperforate inner vessel base 36 which completes the separation of inner vessel 30 from outer vessel upper and lower chambers 22 and 24.

Figure 3:
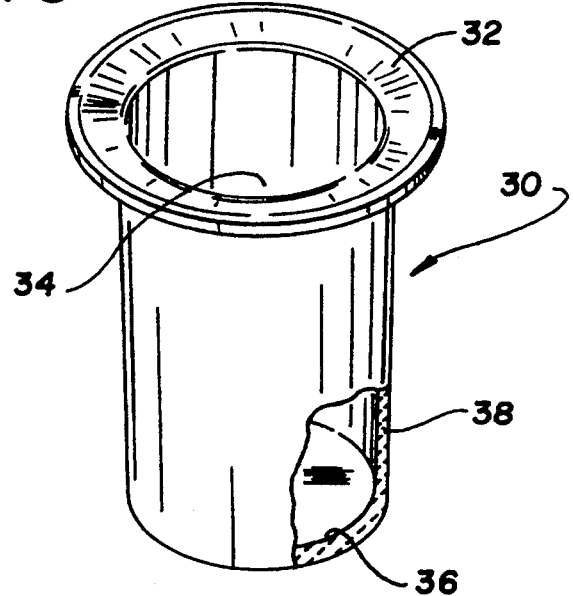
FIG. 3 is a perspective view of the inner vessel.

FIG. 3 shows a perspective view of inner vessel 30. Here flanged collar 32 extends outwardly at the top of imperforate inner vessel wall 38. Imperforate inner vessel wall 38 is connected to imperforate inner vessel base 36 forming inner vessel chamber 34 into which liquid, dirt, plants, flowers, or artificial flowers may be placed.

Figure 4:
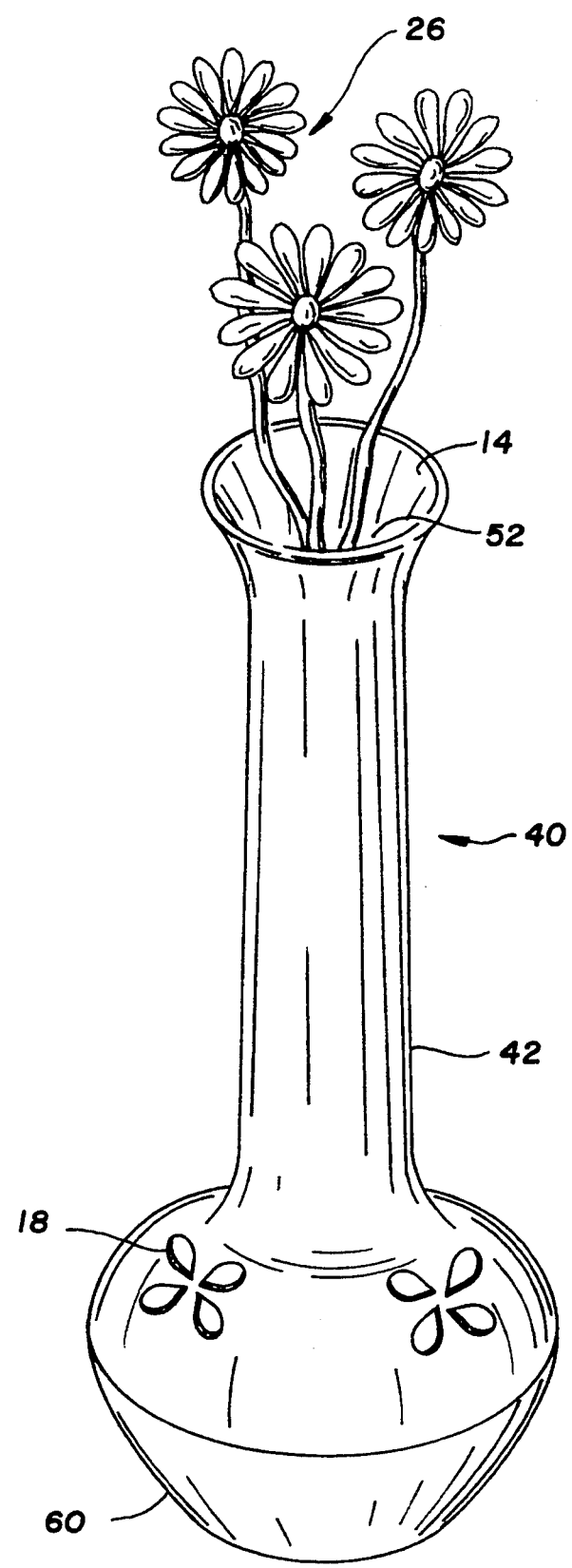
FIG. 4 is a perspective view of an alternate embodiment of the combination vase and air fragrance dispenser.
Figure 5:
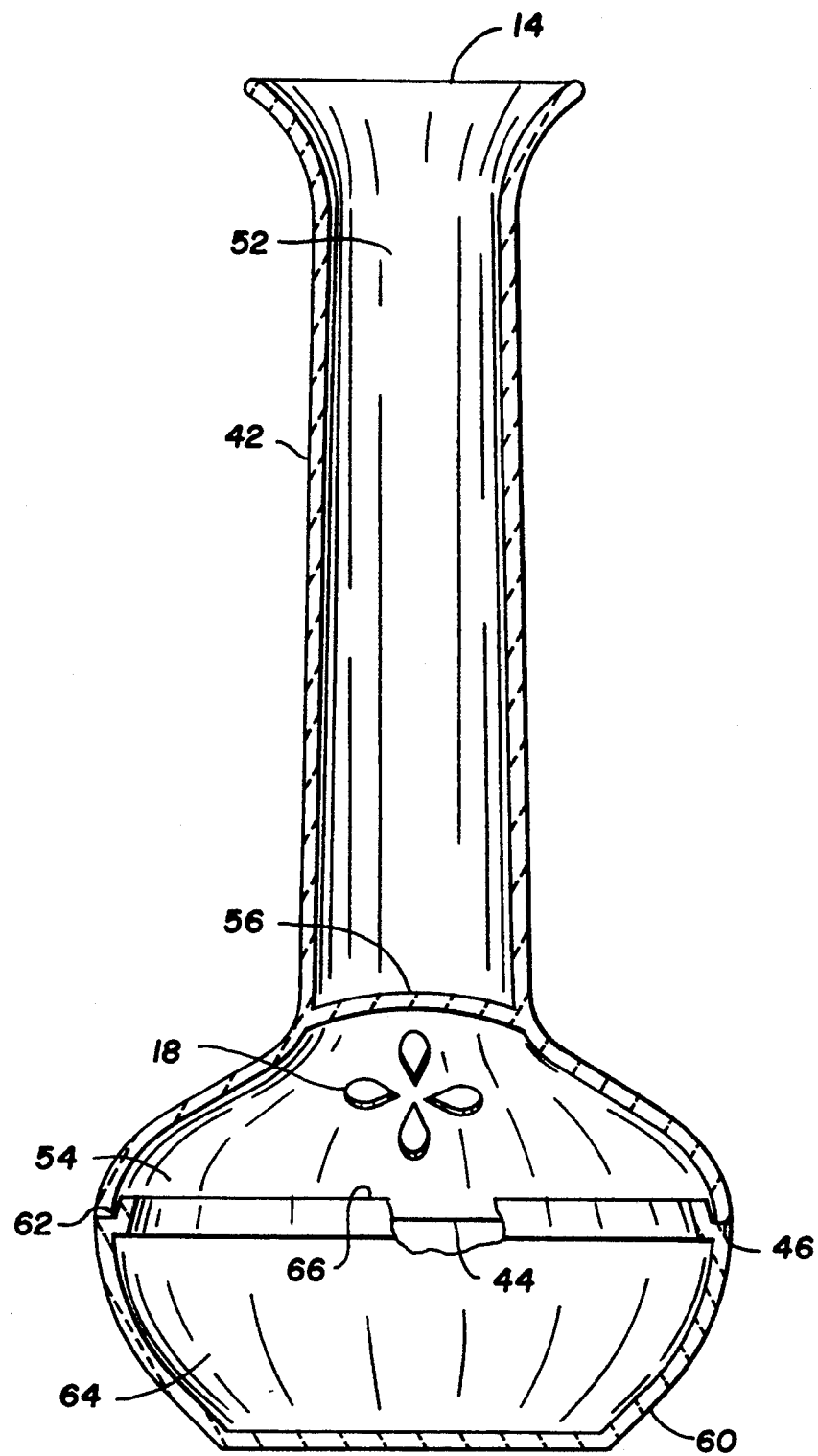
FIG. 5 is a vertical sectional view of the embodiment shown in FIG. 4.

FIGS. 4 and 5 show an alternate embodiment of combination vase and air fragrance dispenser 40. In the description of this embodiment, elements similar to those in FIGS. 1–3 embodiment will be described with the same reference numbers. Thus, as illustrated in FIG. 4, combination vase and air fragrance dispenser 40 is comprised of an upper vessel 42 and a lower vessel 60. Upper vessel 42 has top opening 14 which opens to an upper vessel upper chamber 52 from which flowers 26 protrude upward. A plurality of vent holes 18 are positioned on the lower portion of upper vessel 42.

As shown in FIG. 5, upper vessel 42 is comprised of top opening 14, upper vessel upper chamber 52 into which liquid, flowers, or artificial flowers may be placed and an upper vessel lower chamber 54. Upper vessel lower chamber 54 is divided from upper vessel upper chamber 52 by an imperforate chamber separator 56. Upper vessel lower chamber 54 has a plurality of vent holes 18 to provide venting for fragrance from air treatment material to atmosphere. Lower vessel 60 is bowl-shaped, forming a lower vessel chamber 64 into which liquid or solid air treatment material may be placed. A lower lip 46 of upper vessel 42 sits on an inward flanged collar 62 of lower vessel 60. Lower vessel chamber 64 is thus connected to upper vessel lower chamber 54 through a lower vessel opening 66 and an upper vessel lower opening 44. These form one continuous chamber, enabling the fragrance to rise from the lower vessel 60 and pass through vent holes 18 in upper vessel 42 and then into the atmosphere.

The combination vase and air fragrance dispenser of the present invention provides a readily usable and aesthetically pleasing device which conveniently allows for display of natural or artificial flowers and simultaneously provides for dissipating fragrance into the atmosphere. Its two-vessel construction makes it possible to completely separate flowers and air treatment material, thus preventing contamination of the flowers.

Having thus described an illustrative preferred embodiment and an alternate embodiment incorporating the present invention, it is to be understood that other embodiments may also be used. It is to be understood that all deviations from the illustrative embodiments are to be considered as part of the present invention as set forth in the following claims.

What is claimed is:

1. A vase and air fragrance dispenser comprising,
an outer vessel having a top opening defined by an annular wall, a plurality of vent holes, and an upper and lower chamber with the lower chamber including a bottom wall, said lower chamber providing means for holding a liquid or solid air treatment material, and said upper chamber providing means for venting fragrance from said air treatment material to atmosphere through said vent holes, and
an inner vessel inserted in said top opening of said outer vessel and being suspended from said annular wall with a base of said inner vessel being spaced from said bottom wall, said inner vessel having imperforate side walls and base, and enclosing a chamber providing means for holding liquid, dirt, plants, flowers, or artificial flowers, and means for preventing their passage into said outer-vessel, or passage of said air treatment material into said inner vessel,
whereby said vase and air fragrance dispenser provides a means to attractively display the real or artificial flowers while simultaneously providing means for release of fragrance from said air treatment material and means for complete separation of said air treatment material from said flowers.

2. A vase and air fragrance dispenser comprising,
a lower vessel enclosing a chamber which provides means for holding a liquid or solid air treatment material, and
an upper vessel which fits on top of said lower vessel, said upper vessel having a top opening, a plurality of vent holes, and an upper and lower chamber divided by an imperforate chamber separator, said upper chamber providing means for holding liquid, dirt, plants, flowers, or artificial flowers, said chamber separator providing means for preventing their passage into said lower vessel or passage of said air treatment material into said upper vessel upper chamber, and said lower chamber providing means for venting fragrance from said air treatment material to atmosphere through said vent holes,
whereby said vase and air fragrance dispenser provides a means to attractively display the real or artificial flowers while simultaneously providing means for release of fragrance from said air treatment material and means for complete separation of said air treatment material from said flowers.

* * * * *